US006960190B2

(12) United States Patent
Stinson

(10) Patent No.: US 6,960,190 B2
(45) Date of Patent: Nov. 1, 2005

(54) VACUUM REGULATOR AND METHOD

(75) Inventor: David C Stinson, Richmond Hill, CA (US)

(73) Assignee: Amvex Corporation, Richmond Hill (CA)

( * ) Notice: Subject to any disclaimer, the term of this patent is extended or adjusted under 35 U.S.C. 154(b) by 0 days.

(21) Appl. No.: 10/248,094

(22) Filed: Dec. 18, 2002

(65) Prior Publication Data

US 2004/0122365 A1 Jun. 24, 2004

(51) Int. Cl.[7] .............................................. A61M 1/00
(52) U.S. Cl. ..................................................... 604/119
(58) Field of Search ............................... 604/28, 30–31, 604/35, 500, 503, 505, 506, 514, 65–67, 604/118–121, 245–247, 317–326; 128/205.19, 128/911

(56) References Cited

U.S. PATENT DOCUMENTS

| 4,710,165 | A | * | 12/1987 | McNeil et al. ................. 604/67 |
| 4,795,448 | A | | 1/1989 | Stacey et al. |
| 4,988,336 | A | * | 1/1991 | Kohn ............................ 604/67 |
| 5,419,768 | A | * | 5/1995 | Kayser ......................... 604/119 |
| 5,766,155 | A | | 6/1998 | Hyman et al. |
| 6,162,194 | A | * | 12/2000 | Shipp ........................... 604/151 |
| 2001/0035051 | A1 | * | 11/2001 | Karlicek ....................... 73/708 |
| 2003/0040687 | A1 | | 2/2003 | Boynton et al. |

OTHER PUBLICATIONS

Amvex Corporation Brochure.
Patricia L. Carroll, R.N., (Middletown, CT) The Principles of Vacuum & Its Use in the Hospital Environment.
Brenda Shelton, et al, Medical Applications of Suction—A Nursing Manual, 1985—Puritan Bennett Corporation.
Vacutron Suction Regulator, Operations and Maintenance Guide, Mar. 1989, Allied Healthcare Products, Inc., St. Louis, MO.
Allied Healthcare Products, Inc., Instruments of Care.
Medical Gas Technology product brochure May 2002.
Ohmeda Product Information, Madison, WI.
Precision Medical User Manual, Nov. 1999, Northampton, PA.
Boehringer Suction Regulators Operating and Maintenance Instructions, 1992 Norristown, PA.
Boehringer Suction Regulators Information Brochure, 1998 Norristown, PA.

* cited by examiner

Primary Examiner—Nicholas D. Lucchesi
Assistant Examiner—Matthew F. DeSanto
(74) Attorney, Agent, or Firm—Edward W. Goebel, Jr.; Jon L. Woodard; MacDonald Illig Jones & Britton

(57) ABSTRACT

A vacuum pressure regulator system for use in association with a vacuum system in which a vacuum is employed for healthcare purposes, for assisting in monitoring and regulating the vacuum pressure, and having a manual pressure control valve to adjust the treatment vacuum pressure supplied to the patient, a vacuum pressure sensor to sense the treatment vacuum pressure for the patient in the system, and producing a treatment vacuum pressure signal, a sampling circuit which intermittently samples the pressure signal generated by the pressure sensor and generate sampling signals, an electrically powered pressure display circuit, and digital pressure display, for receiving the sampling signals and providing a visible display, and, a non-mains power supply.

8 Claims, 4 Drawing Sheets

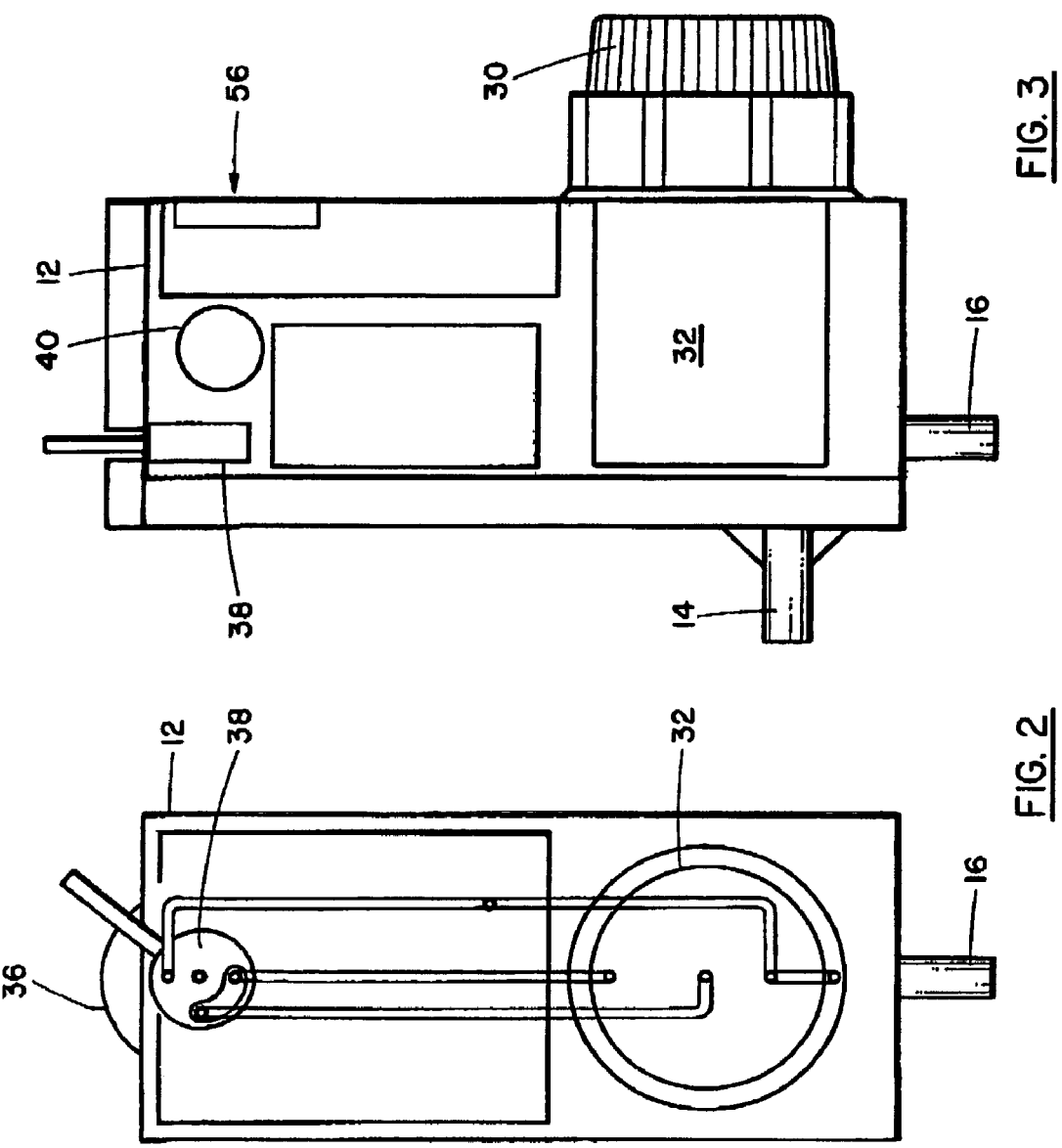

VACUUM REGULATOR AND METHOD

BACKGROUND OF INVENTION

The invention relates to medical and hospital healthcare vacuum systems and in particular to a vacuum pressure gauge and regulator having a solid state, non-mains powered sensor for monitoring the vacuum pressure and enabling the operator to maintain a stable level of vacuum for administration to a patient, and to a vacuum regulator incorporating such a vacuum pressure gauge.

In the field of health care, vacuum systems are required in many circumstances. A vacuum may be required to be applied to a patient for a variety of reasons.

In these cases care must be taken to ensure that the level of vacuum negative pressure is maintained at the level required for a particular treatment. To do this manual controls, known as vacuum regulators, are provided by which the level of vacuum pressure can be controlled and varied.

Pressure gauges are also provided either incorporated in or matched with the vacuum regulator which monitor the level of vacuum pressure.

In the past the mechanical systems in such vacuum regulators for actually varying and controlling the vacuum used simple vent valves and the like. Such valves could be controlled manually usually by a control knob. The pressure gauge was usually a mechanical type gauge, which consisted of a pressure sensor with a dial, and a needle showing the pressure. An operator would glance at the dial and needle from time to time to ensure that the vacuum level remained stable at the desired pressure.

Such known pressure gauge systems have been somewhat primitive.

Usually known vacuum regulators used a simple mechanical type pressure gauge with a needle type readout dial showing the pressure. An operator would monitor the gauge reading and might adjust the manual pressure control as desired. This system was somewhat old fashioned for the hospital environment, and was not always practical in emergency situations, for example in a paramedic environment, at an accident scene for example, or in an ambulance. For example, the dial and needle may require to be checked repeatedly, and it was possible for the paramedic to misread the dial.

Such known systems were also capable of providing for intermittent vacuum pulses to be supplied at intervals.

The intermittent control in many cases was difficult to maintain and difficult to regulate as to timing.

U.S. Pat. No. 4,988,336 issued Jan. 29, 1991, G. S. Kohn, discloses a complex vacuum pressure regulator in which the vacuum source is used to drive a rotary air powered motor which in turn drives an electrical generator, which is part of the regulator. The vacuum control valve is electrically operated and turns the vacuum on and off for intermittent supply of vacuum to the patient. This system is unnecessarily complex in that it incorporates its own electrical generator, and uses that generator to power the electronic on/off switching of the vacuum.

U.S. Pat. No. 5,419,768 issued May 30, 1995, J. P. Kayser discloses a vacuum regulator in which the actual vacuum control valve is operated by a solenoid. The solenoid is programmed to open and close the valve automatically for intermittent operation. This system is also complex, and would consume a considerable power supply.

There is a need for a vacuum pressure regulator having a more precise pressure readout, preferably one that provides a better visual readout, such as could be provided by a digital numeral LCD display.

Preferably such a system will be independent of mains power, and will be a system that is solid state operated, with battery power, for most applications, thus permitting it to be used anywhere in a facility or in the field if needed. Preferably the vacuum pressure display will be incorporated in the body of a manual vacuum pressure regulator, so that the digital vacuum pressure display is provided in a single compact unit.

Preferably there will also be an alarm, of some form, incorporated in the pressure gauge which will alert the attendant if there is a loss of vacuum.

Preferably the pressure regulator will be designed to operate on a minimum of power, so that it can be powered by a long life battery, a rechargeable battery, a 12 volt battery, or by solar power if desired. Mains power connections could also be incorporated, so as to be available to be used, when required, as an optional alternative supply.

The regulator control will preferably incorporate a potentiometer connected to the logic so that when the control knob is rotated to adjust the pressure, the sampling rate is increased temporarily. This will give an instantaneous readout, on the display of the new pressure.

SUMMARY OF INVENTION

With a view to providing the foregoing advantages, the invention comprises a vacuum pressure regulator system for use in association with a vacuum system in which a vacuum is employed for healthcare purposes, for assisting in monitoring and regulating the vacuum pressure, and which vacuum pressure regulator system has a manual pressure control valve operable by an operator to adjust the treatment vacuum pressure supplied to the patient, a vacuum pressure sensor operable to sense the treatment vacuum pressure for the patient in the system, and to produce a treatment vacuum pressure signal, a sampling circuit operable intermittently by electrical power to sample said pressure signal generated by said pressure sensor at predetermined time intervals and generate sampling signals, an electrically powered pressure display circuit, and digital pressure display, for receiving said sampling signals and generating a visible digital pressure display, and, a non-mains power supply connected for supplying power both to said sampling circuit for sampling said vacuum sensor, and to said display circuit and said digital display.

The invention further seeks to provide such a vacuum pressure regulator including a no-pressure signal generator for generating at least one no-pressure signal representing an absence of treatment vacuum pressure, and an alarm signal generator, and an alarm responsive thereto, operable in response to a no-pressure signal to generate an alarm.

The invention further provides such a vacuum pressure regulator system in which said regulator is manually operable to adjust said treatment vacuum pressure so as to maintain a desired level of vacuum pressure.

The invention further provides such a vacuum pressure gauge system in which said no-pressure signal generator responds to the occlusion of a treatment device connected to a patient and signals an alarm.

The invention further provides such a vacuum pressure regulator system in which an operator override control is provided whereby an operator can manually override said pressure control valve and supply full vacuum for treatment of said patient.

The vacuum applied to the patient may be and usually is, connected to the patient through a know collection bottle, and material removed from the patient may be allowed to collect in such a collection bottle thus preventing the material from being withdrawn up into the vacuum system itself.

The invention also provides a method of supplying and regulating a vacuum to a patient, with a non-mains powered regulator, and sampling the vacuum pressure at timed intervals so as to conserve power.

The various features of novelty which characterize the invention are pointed out with more particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

BRIEF DESCRIPTION OF DRAWINGS

FIG. 2 is a sectional illustration of a vacuum pressure regulator of FIG. 1 along line 2—2 of FIG. 1;

FIG. 3 is a conduit diagram illustrating the layout of the various conduits connecting the components of the pressure regulator of FIG. 1;

DETAILED DESCRIPTION

Figure 1:
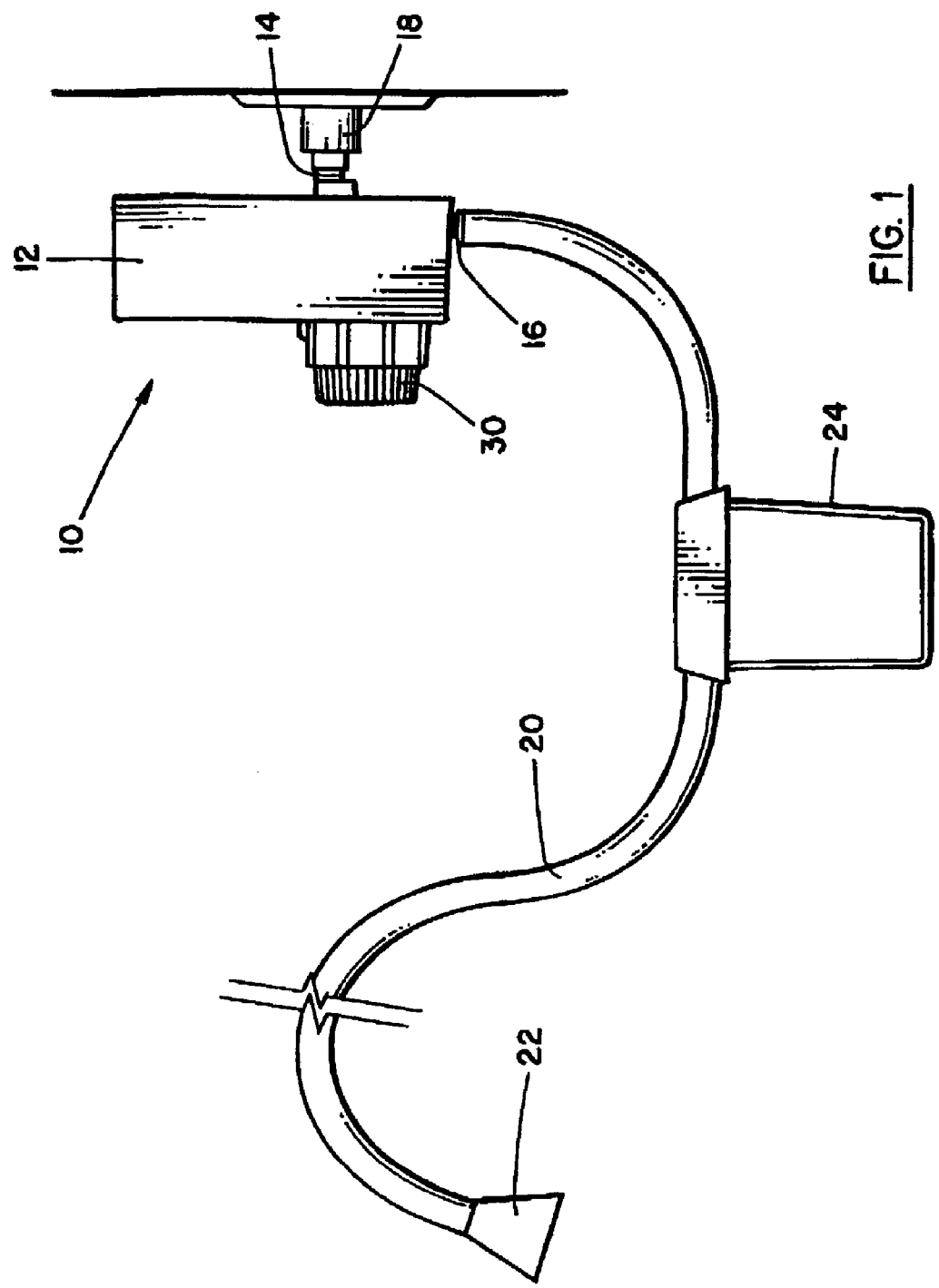
FIG. 1 is a schematic view of a vacuum pressure system, showing the vacuum pressure regulator illustrating the invention.

Referring to FIG. 1 it will be seen that the invention is there illustrated in the form of a vacuum regulator (10) having a housing (12), a vacuum source connection (14), and a vacuum patient connection (16). Typically the vacuum connection (14) will be connected to a known vacuum conduit (18) common in many hospitals, and paramedical vehicles. The conduit, in a hospital is located in or on a wall, and has connection points in various rooms, by means of which a paramedic, doctor or nurse, may have quick access to a source of vacuum wherever required. The patient connection (16) may be connected by a patient hose (20) to a vacuum tube or device (not shown), by means of which the patient may be treated with a vacuum in any desired circumstances.

Typically a collector bottle (24) is provided in the patient hose, for collecting any mucous or other material removed from the patient via the hose.

Referring to FIGS. 2 and 3 the components within the vacuum regulator housing are seen in more detail. On the housing (12) there is a manually operable control knob (30) connected to a pressure control valve (32) within housing (12). By operation of knob (30) the vacuum pressure can be adjusted, manually, as desired. Knob (30) is coupled with a control sensor, in this case a potentiometer ring (31) known per se (FIG. 4), for reasons described below.

The vacuum regulator (10) has a visual indicator or window (34) for a display (described below), on which the treatment vacuum pressure is displayed, and also has an alarm (36). The alarm may be a flashing light, or an audible buzzer or a combination of warning alert devices.

A mode select switch (38) is operable to select either automatic regulation or manual override, as desired.

In accordance with the invention a power source, in this case a battery (40) is located within housing (12) and is connected to a circuit board of the vacuum sensor as will be described below. Other forms of power source could replace the battery or could be combined with the battery, a rechargeable storage device, solar power, or a mains power supply and transformer.

Figure 4:
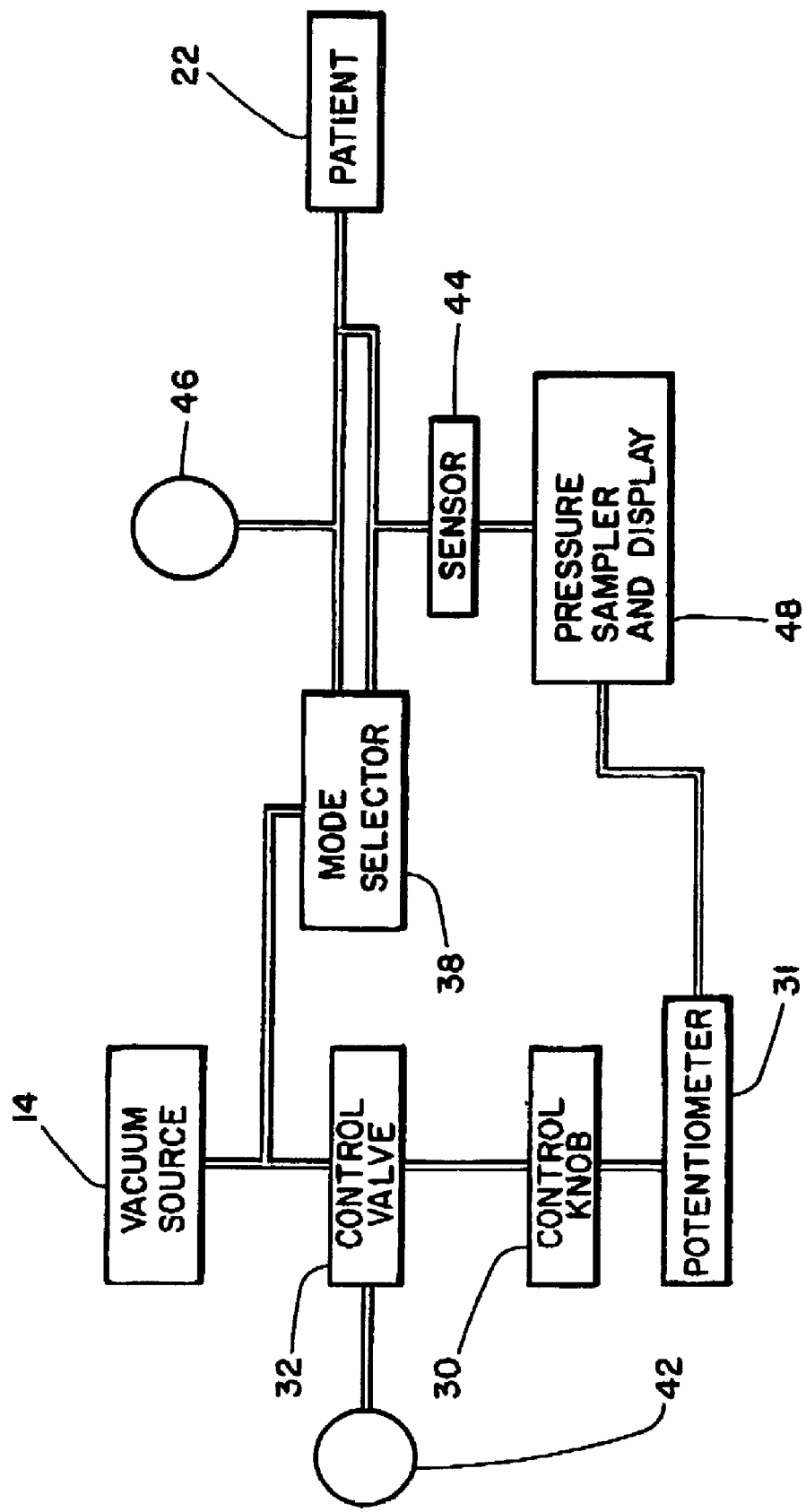
FIG. 4 is a block diagram illustrating the connection of the mechanical components of the vacuum pressure controls FIG. 1; and, FIG. 5 is a block circuit diagram of the vacuum pressure sensor and display.

FIG. 4 illustrates the vacuum conduit connections within the housing (12) between the various mechanical components, corresponding to FIG. 3, but in schematic form.

The vacuum source (14) is shown connected to the control valve (32). The valve (32) is connected to a vent, to atmosphere (42) for allowing entry of air to reduce the vacuum pressure with the system. Such control valves are known, and the details are not shown for the sake of clarity. The control knob (30) connects to the control valve for manual operation and adjustment of the control valve by an operator. This permits the operator to manually adjust the level of vacuum being supplied to the patient.

The mode selection control (38) allows an operator to select either an off position or an automatic operation position, of the control valve, or manual override position, which cuts out the control valve and applies full vacuum to the patient.

A pressure sensor (44) senses the vacuum pressure and provides a pressure signal.

Figure 5:
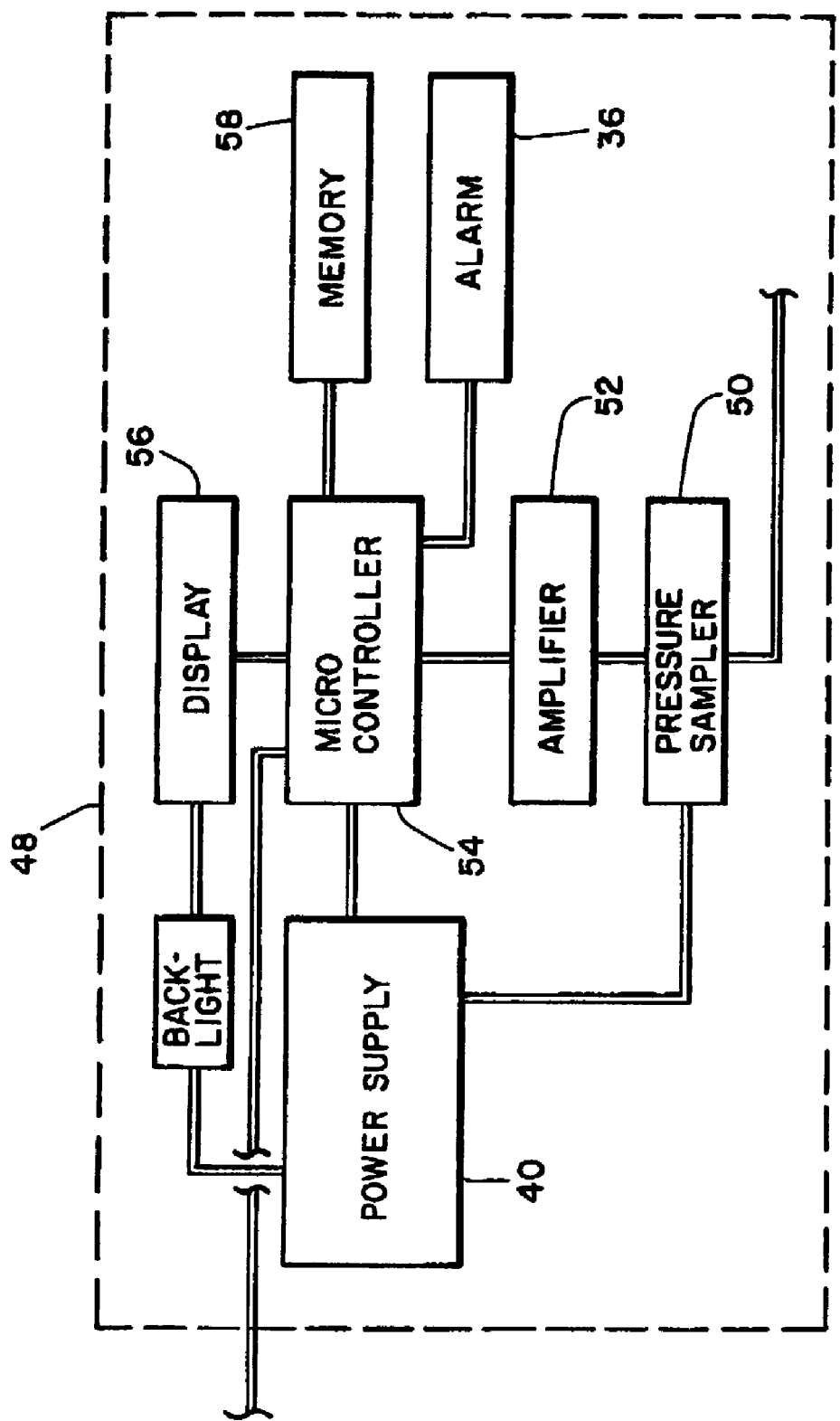

FIG. 5 illustrates the electronic circuit by which the pressure signal is sampled at intervals. A further vent (46) is provided in the line connection to the patient. A sampler circuit (48) is located in housing (12), which is described below.

A pressure sampler (50) is connected to the pressure sensor (44), and operates at intervals to sample the pressure detected in the pressure sensor. Sampler (50) is powered by power supply (40). This can be anyone of, or a combination of the various different power supplies listed above.

Pressure sampler (50) is connected to amplifier (52) to amplify the pressure signal.

Amplifier (52) is connected to micro controller (54). Controller (54) is connected to a digital display, typically an LCD display, shown as (56). Display (56) is located in window 44 above. The controller (54) is also connected to the potentiometer of control knob (30). The controller (54) controls the sampler (50) which then samples the pressure at predetermined time intervals. This provides a read out on the display (56) each time a sample is taken. This greatly reduces the power consumption of the system. Thus, a power supply in the form of a long-life battery will provide extended operation, without the need for a mains connection.

The sampling rate can be changed by the controller (54). Thus, as the control knob (30) is rotated, the controller (54) will temporarily increase the sampling rate of the sampler (50). In this way the display will give an instantaneous reading of the new pressure setting.

A memory (58) is connected to controller (54).

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. The method of regulating a vacuum treatment to a patient supplied from a vacuum sources by means of a non-mains powered vacuum regulator and comprising:
   sensing the pressure of vacuum being supplied to the patient, at regular time intervals, so as to conserve power, and generating pressure signals thereby;
   supplying said pressure signals to a display, whereby the pressure of said vacuum can be monitored;
   manually operating a control valve to control said vacuum pressure; and
   sensing a change in the position of said manual control, and generating a control signal thereby and said control signal varying said intervals of said intermittent pressure sensing, whereby to provide an instantaneous display of pressure.

2. A method as claimed in claim 1 including providing circuitry powered by a mains power supply with a transformer.

3. The method of regulating a vacuum treatment to a patient supplied from a vacuum source by means of a non-mains powered vacuum regulator and comprising:
   sensing the pressure of vacuum being supplied to the patient, at regular time intervals, and generating pressure signals thereby;
   supplying said pressure signals to a display, whereby the pressure of said vacuum can be monitored;
   manually operating a control valve to control said vacuum pressure; and
   sensing a change in the position of said manual control, and generating a control signal thereby and said control signal varying said intervals of said intermittent pressure sensing, whereby to provide an instantaneous display of pressure.

4. The method of regulating a vacuum treatment to a patient supplied from a vacuum source as claimed in claim 3 and including sensing an absence of vacuum pressure and generating an alarm signal thereby.

5. The method of regulating a vacuum treatment to a patient supplied from a vacuum source as claimed in claim 4 and including operating an override switch whereby to override said venting of said vacuum pressure, and to supply full vacuum pressure to said patient.

6. A method of regulating the level of vacuum administered to a patient comprising:
   (a) adjusting a pressure control valve to a selected vacuum administered to said patient;
   (b) intermittently sensing said vacuum with circuitry to general signals in response thereto;
   (c) supplying said generated signals to a display to digitally display said level of vacuum;
   (d) powering said circuitry by a battery;
   (e) amplifying said intermittently sensed vacuum;
   (f) including a micro controller in the circuitry for generating said signals to said display;
   (g) reducing power requirements from said battery when said micro processor intermittently senses said vacuum;
   (h) generating an alarm when said microprocessor senses an absence of vacuum;
   (i) manually adjusting said pressure control valve;
   (j) intermittently sensing said vacuum at a pre-selected time interval; and
   (k) temporarily increasing said time interval when manually adjusting said pressure control valve.

7. A method as claimed in claim 6 including the step of manually overriding said pressure control valve to supply full vacuum to said patient.

8. A method as claimed in claim 7 including saving said generated signals in memory.

* * * * *